United States Patent [19]

Fujiwara et al.

[11] 4,329,339

[45] May 11, 1982

[54] ANTHRACYCLINONES AND DERIVATIVES THEREOF

[75] Inventors: Akiko Fujiwara; Tatsuo Hoshino, both of Kamakura; Masaaki Tazoe, Yokohama, all of Japan

[73] Assignee: Hoffmann-La Roche Inc., Nutley, N.J.

[21] Appl. No.: 152,003

[22] Filed: May 21, 1980

[51] Int. Cl.³ .................. A61K 31/71; C07H 15/26
[52] U.S. Cl. ............................ 424/180; 424/181; 435/78; 536/6.4; 260/365
[58] Field of Search .............. 536/17 A; 424/181, 180

[56] References Cited

U.S. PATENT DOCUMENTS 3,988,315  10/1976  Umezawa et al. ............... 536/17 A

OTHER PUBLICATIONS

Asheshov et al., "Biochem. Jour.", 81, 1961, pp. 101–104.
Oki et al., "The Jour. of Antibiotics", vol. 28, 1975, pp. 830–834.

Primary Examiner—Johnnie R. Brown
Attorney, Agent, or Firm—Jon S. Saxe; Bernard S. Leon; Frank P. Hoffman

[57] ABSTRACT

There is disclosed compounds of the formula

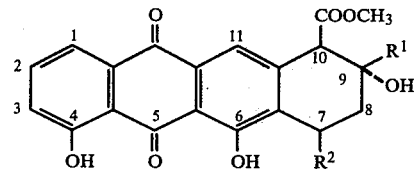

wherein $R^1$ represents a methyl or acetonyl group and $R^2$ represents a hydrogen atom, a hydroxyl group or a group of the formula

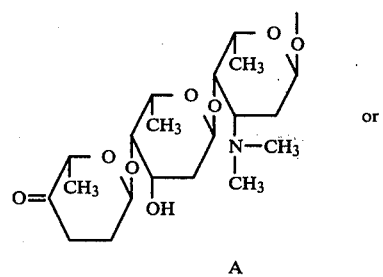

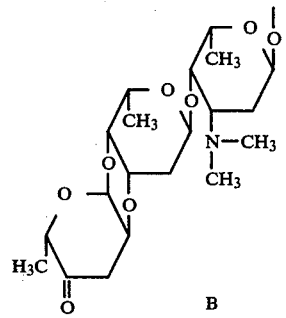

and a process for the preparation thereof.

The compounds are useful as intermediates for the preparation of anthracycline antibiotics and certain of the compounds exhibit per se activity as antibacterial and antitumor agents.

6 Claims, No Drawings

ANTHRACYCLINONES AND DERIVATIVES THEREOF

DESCRIPTION OF THE INVENTION

The present invention relates to novel tetracyclic compounds, to a process for the preparation thereof, to pharmaceutical preparations containing those compounds which are effective against tumors and to novel microorganisms used in this process.

More particularly, the present invention is concerned with novel anthracyclinones and derivatives thereof which are compounds of the formula

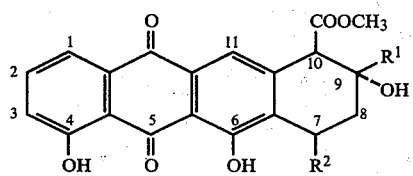

wherein $R^1$ represents a methyl or acetonyl group and $R^2$ represents a hydrogen atom, a hydroxyl group or a group of the formula

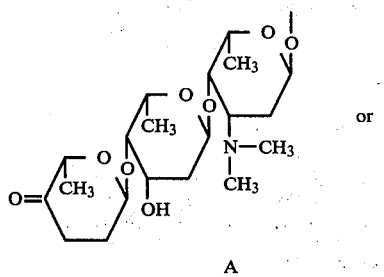

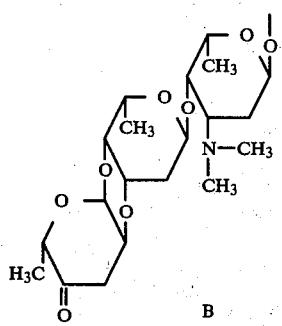

In this description and in the claims appended hereto the specific compounds encompassed by formula I are named as follows:

| $R^1$ | $R^2$ | Compound |
|---|---|---|
| —$CH_3$ | H | 7-Deoxyauramycinone |
|  | OH | Auramycinone |
|  | A | Auramycin A |
|  | B | Auramycin B |
| —$CH_2$—CO—$CH_3$ | H | 7-Deoxysulfurmycinone |
|  | OH | Sulfurmycinone |
|  | A | Sulfurmycin A |
|  | B | Sulfurmycin B |

The novel compounds provided by the present invention are characterised by the following physico-chemical data. [The solvents used in thin-layer chromatography (TLC) are chloroform/methanol, 10:1, v/v (solvent A); chloroform/methanol, 100:1, v/v (solvent B); toluene/methanol, 10:1, v/v (solvent C) and toluene/methanol, 30:1, v/v (solvent D)]:

Auramycin A ($C_{41}H_{51}O_{15}N$)
MW: 797.3
Melting point: 141° C. (decomposition)
Specific rotation: $[\alpha]_D^{20}=8.0°$ (c=0.1 in chloroform)
TLC (silica gel): $R_f$ 0.45 (solvent A) $R_f$ 0.21 (solvent C)

Auramycin B ($C_{41}H_{49}O_{15}N$)
MW: 795.3
Melting point: 161° C. (decomposition)
Specific rotation: $[\alpha]_D^{20}=-8.0°$ (c=0.1 in chloroform)
TLC (silica gel): $R_f$ 0.66 (solvent A) $R_f$ 0.43 (solvent C)

Sulfurmycin A ($C_{43}H_{53}O_{16}N$)
MW: 839.3
Melting point: 140° C. (decomposition)
Specific rotation: $[\alpha]_D^{20}=-23.3°$ (c=0.1 in chloroform)
TLC (silica gel): $R_f$ 0.39 (solvent A) $R_f$ 0.15 (solvent C)

Sulfurmycin B ($C_{43}H_{51}O_{16}N$)
MW: 837.3
Melting point: 149° C. (decomposition)
Specific rotation: $[\alpha]_D^{20}=-21.5°$ (c=0.1 in chloroform)
TLC (silica gel): $R_f$ 0.61 (solvent A) $R_f$ 0.38 (solvent C)

Auramycinone ($C_{21}H_{18}O_8$)
MW: 398.1
Melting point: 153.5° C.
Specific rotation: $[\alpha]_D^{20}=+178.0°$ (c=0.1 in chloroform)
TLC (silica gel): $R_f$ 0.24 (solvent B) $R_f$ 0.32 (solvent D)

Sulfurmycinone ($C_{23}H_{20}O_9$)
MW: 440.1
Melting point: 159° C.
Specific rotation: $[\alpha]_D^{20}=+232.2°$ (c=0.1 in chloroform)
TLC (silica gel): $R_f$ 0.28 (solvent B) $R_f$ 0.28 (solvent D)

7-Deoxyauramycinone ($C_{21}H_{18}O_7$)
MW: 382.1
Melting point: 200° C.
Specific rotation: $[\alpha]_D^{20}=+81.2°$ (c=0.1 in chloroform)
TLC (silica gel): $R_f$ 0.32 (solvent B) $R_f$ 0.44 (solvent D)

7-Deoxysulfurmycinone ($C_{23}H_{20}O_8$)
MW: 424.1
Melting point: 219.5° C.
Specific rotation: $[\alpha]_D^{20}=+73.9°$ (c=0.1 in chloroform)
TLC (silica gel): $R_f$ 0.49 (solvent B) $R_f$ 0.60 (solvent D)

According to the process provided by the present invention, the novel compounds of formula I hereinbefore are prepared by (a) cultivating a microorganism belonging to the species Streptomyces galilaeus capable of producing the compounds of formula I in an aqueous nutrient medium under aerobic conditions and recovering said compounds from the fermentation broth, (b) hydrolysing under acidic conditions a compound of the general formula

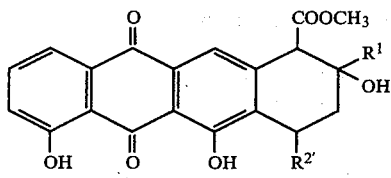

wherein $R^1$ has the significance given earlier and $R^{2'}$ represents a group of formula A or B hereinbefore, to convert the group $R^{2'}$ into a hydroxyl group, or (c) splitting off the sugar moiety from a compound of formula I' by means of a catalyst or an enzyme to replace the group $R^{2'}$ in formula I' by a hydrogen atom.

The microorganism used in embodiment (a) of the foregoing process includes all strains belonging to the species Streptomyces galilaeus capable of producing the compounds of formula I, including mutants and variants thereof. Preferred strains are Streptomyces galilaeus OBB-111 and Streptomyces galilaeus FR-401 which have been isolated from soils in Neuschwanstein and Murnau respectively, Oberbayern, West Germany, as well as mutants and variants thereof, preferably Streptomyces galilaeus OBB-111-610, obtained by treating Streptomyces galilaeus OBB-111 with N-methyl-N'-nitro-N-nitrosoguanidine. Such mutants can be obtained from the parent strains by normal mutation methods; for example, by irradiation with UV light, X-rays or γ-rays, or by treatment with suitable mutagens. The strains Streptomyces galilaeus OBB-111, Streptomyces galilaeus OBB-111-610 and Streptomyces galilaeus FR-401 which also form part of the present invention have been deposited in the Agency of Industrial Science and Technology, Fermentation Research Institute, Japan, under FERM-P No. 4780 (Jan. 29, 1979), FERM-P No. 4883 (Mar. 22, 1979) and FERM-P No. 4882 (Mar. 22, 1979) respectively, and at the American Type Culture Collection, Rockville, Md., USA under ATCC Nos. 31533, 31534 and 31535 respectively.

The mycological characteristics thereof are as follows:

1. Morphological properties

The strain OBB-111 (FERM-P No. 4780, ATCC 31533) forms moderately long aerial mycelium from substrate mycelium. Hooks or spirals are observed to develop at the apex of the aerial mycelium, but no whorls are formed.

Mature spore chains with more than 10 spores per chain are usually produced. The spores are cylindrical, measure 0.5 to 0.6μ×0.8 to 1.0μ and their surface is smooth.

The strain FR-401 (FERM-P No. 4882, ATCC 31535) forms aerial mycelium, branched like tufts, from substrate mycelium. Spirals are observed to develop, but no whorls are formed. Mature spore chains with more than 10 spores per chain are usually produced. The spores are cylindrical or ellipsoidal, measure 0.6 to 0.8μ×0.8 to 1.2μ and their surface is smooth.

2. Culture characteristics on various media

The culture characteristics of strains OBB-111 and FR-401 are shown in Table 1 hereinafter:

The colour of the growth of strains OBB-111 and FR-401 on sucrose-nitrate agar, glycerol-asparagine agar, starch-inorganic salts agar and oatmeal agar changes to pink-violet with the dropwise addition of 0.05 N sodium hydroxide solution.

TABLE 1

Culture characteristics of strain OBB-111 and strain FR-401

| Medium | Strain OBB-111 | Strain FR-401 |
|---|---|---|
| Sucrose-nitrate agar | | |
| Growth | dull orange (4pe, Orange Rust) | brown (6ni, Taupe Brown)~pale reddish orange (6ie, Redwood) |
| Aerial Mycelium | brownish gray (3cb, Sand)~pale orange (5cb) | pinkish white (6ge, Rose Gray) |
| Diffusible Pigment | reddish | reddish |
| Glucose-asparagine agar | | |
| Growth | dull orange (3pe, Topaz~3ne, Topaz) | pale orange (4ge, Rose Beige) |
| Aerial Mycelium | light brownish gray (3dc, Natural) | none |
| Diffusible Pigment | brownish | brownish |
| Glycerol-asparagine agar (ISP medium No. 5) | | |
| Growth | pale yellow~pale yellowish brown (3gc, Light Tan~3lc, Amber) | dull reddish orange (5le, Rust Tan~5ne Tile Red) |
| Aerial Mycelium | light gray (2fe, Covert Gray) | light gray (2fe, Covert Gray) |
| Diffusible Pigment | none | brown |
| Starch-inorganic salts agar (ISP medium No. 4) | | |
| Growth | pale yellow (2pc, Brite Gold)~dull yellow (2pe, Mustard Gold) | grayish yellow (3ec, Bisque)~pale yellowish brown (3ge, Lt Tan) |
| Aerial Mycelium | light brownish gray (2dc, Natural)~light gray (2fe, Covert gray) | light brownish gray (3dc, Natural) |
| Diffusible Pigment | yellow | brownish |
| Tyrosine agar (ISP medium No. 7) | | |
| Growth | dark brownish gray (3ni, Clove Brown) | brownish violet (4pe, Dk spice Brown) |
| Aerial Mycelium | none | light gray (3fe, Silver Gray) |
| Diffusible Pigment | black | brown |
| Nutrient agar | | |
| Growth | colourless~pale brown | colourless~pale brown |
| Aerial Mycelium | none | none |
| Diffusible Pigment | none | none |
| Yeast extract-malt extract agar (ISP medium No. 2) | | |
| Growth | yellowish brown (3ng, Yellow Maple) | pale yellowish brown (3ie, Camel) |
| Aerial Mycelium | light gray (2fe, Covert Gray) | light gray (2fe, Covert Gray)~light brownish gray (3dc, Natural) |
| Diffusible Pigment | none | none |
| Oatmeal agar (ISP medium No. 3) | | |
| Growth | pale yellowish brown (2gc, Bamboo)~pale brown | pale yellowish brown (3ie, Camel)~pale reddish |
| | brown (4ge, Nude (3ie, Camel) | Tan |
| Aerial Mycelium | light gray (2fe, Covert Gray~3fe, Silver Gray) | light grayish reddish brown (5fe, Ashes) |
| Diffusible Pigment | brown | red |
| Skimmed milk (37° C.) | | |
| Growth | brown~dark brown | brown~dark brown |

TABLE 1-continued

| Medium | Strain OBB-111 | Strain FR-401 |
|---|---|---|
| Aerial Mycelium | white~brownish gray | none |
| Diffusible Pigment | dark brown | dark brown |
| Glucose peptone gelatin stab | | |
| Growth | pale yellow | colourless |
| Aerial Mycelium | none | none |
| Diffusible Pigment | brown | brown |

Culture characteristics of strain OBB-111 and strain FR-401

3. Physiological characteristics

The physiological characteristics and carbohydrate utilisation of the strains OBB-111 and FR-401 are shown in the following Tables 2 and 3, respectively. The growth temperature was examined on yeast extract-malt extract agar (ISP medium No. 2) at 5°, 20°, 27°, 32°, 37°, 45° and 55° C. The optimal temperature for growth is 27° C. to 32° C. and no growth occurs at 5°, 45° and 55° C.

TABLE 2

Physiological characteristics of strain OBB-111 and strain FR-401

| Test | Response | Methods and Material Used |
|---|---|---|
| Gelatin liquefaction | moderate liquefaction | glucose-peptone-gelatin medium; 27° C. |
| Starch hydrolysis | weak to moderate hydrolysis | starch-inorganic salts agar |
| Peptonisation and coagulation of skimmed milk | moderate to strong peptonisation and no coagulation | 10% skimmed milk; 37° C. |
| Nitrate reduction | positive | ISP medium No. 8; 27° C. |
| Melanin formation | positive | ISP medium No. 1 ISP medium No. 6 ISP medium No. 7 |

TABLE 3

Carbohydrate utilisation of strain OBB-111 and strain FR-401

| L-Arabinose | positive |
|---|---|
| D-Xylose | positive |
| Glucose | positive |
| D-Fructose | positive |
| Sucrose | positive |
| Inositol | positive |
| L-Rhamnose | positive |
| Raffinose | positive |
| D-Mannitol | negative |

Basal medium: Pridham-Gottlieb medium (ISP medium No. 9)
Temperature: 27° C.

The foregoing characteristics of strains OBB-111 and FR-401 can be summarised as follows: The strains belong to the genus Streptomyces. The aerial mycelium forms spirals at the apex but no whorls. The surface of the spores is smooth. The growth on various media is found to be pale yellowish brown to pale brown or dull orange, and the aerial mycelium is light grey. The strains produce reddish to brown diffusible pigment and melanin on various media. Among known species of Streptomyces, strains OBB-111 and FR-401 resemble *Streptomyces galilaeus* (Reference 1: Archiv für Mikrobiologie, 31, 356, 1958. Reference 2: The Actinomycetes, 2, 215, 1961. Reference 3: International Journal of Systematic Bacteriology, 22, 298, 1972) and *Streptomyces galilaeus* MA 144-M1, FERM-P No. 2455 (Reference 1: Japanese Patent Publication No. 34915/1976). The differences between the present strains and the standard strains of *S. galilaeus* ISP 5481 and *S. galilaeus* MA 144-M1 (FERM-P No. 2455) were investigated by parallel cultures. The results are shown in Table 4 hereinafter.

TABLE 4

| | OBB-111 and FR-401 | S. galilaeus ISP 5481 | S. galilaeus MA 144-M1 (FERM-P No. 2455) |
|---|---|---|---|
| Liquefaction of gelatin | moderate | weak to moderate | weak to moderate |
| Coagulation of milk | negative | weak positive | negative |
| Diffusible pigment | dark brown | light brown | dark brown |
| Change of colour of growth by 0.05N sodium hydroxide solution: | | | |
| ISP medium No. 3 | pink to violet | — | pink to violet |
| ISP medium No. 4 | slight pink ~violet | — | slight pink ~violet |
| ISP medium No. 5 | violet | slight violet | violet |

From the results the present strains, OBB-111 and FR-401, differ from *S. galilaeus* MA 144-M1 (FERM-P No. 2455) in the liquefaction of gelatin and from *S. galilaeus* ISP 5481 in the coagulation of skimmed milk, the production of diffusible pigment and the change in the colour of growth by 0.05 N sodium hydroxide solution. However, the present strains are very similar to *S. galilaeus* ISP 5481 and *S. galilaeus* MA 144-M1 (FERM-P No. 2455) in morphology and colour of the growth and mycelium on various media, chromogenicity and utilisation of carbohydrates.

However, neither *S. galilaeus* ISP 5481 nor S. galilaeus MA 144-M1 (FERM-P No. 2455) can produce the compounds of formula I.

According to a preferred aspect of embodiment (a) of the foregoing process, the compounds of formula I can be produced by cultivating Streptomyces galilaeus OBB-111, Streptomyces galilaeus OBB-111-610 (FERM-P No. 4883, ATCC 31534) or Streptomyces galilaeus FR-401 in an aqueous nutrient medium under aerobic conditions.

The cultivation may be carried out in a culture medium containing the usual nutrient substances. The carbon sources, for example, are glucose, sucrose, starch, lactose, maltose, fructose, glycerol, dextrin or mixtures thereof and the nitrogen sources are, for example, soyabean meal, cotton seed meal, meat extract, fish meal, peptone, dried yeast, cornsteep liquor, preferably wheat germ or mixtures thereof. Furthermore, if necessary, the culture medium may contain suitable inorganic substances such as phosphates, sulphates, chlorides, bromides, nitrates and carbonates of sodium, potassium, ammonium, calcium and the like.

The cultivation may be carried out in an aqueous medium under aerobic conditions, especially by a submerged fermentation process. The preferred temperature for the cultivation is in the range of 20° C. to 37° C., in particular 25° C. to 30° C. The pH of the medium may vary, but it is generally in the range of 5-8.

After the cultivation has been carried out for about 2 to 10 days under the conditions mentioned earlier, the compounds of formula I can be obtained in the fermentation broth. The compounds of formula I thus obtained, i.e. auramycins A and B, sulfurmycins A and B, auramycinone, sulfurmycinone, 7-deoxyauramycinone and 7-deoxysulfurmycinone, may be recovered from the fermentation broth; for example, by extraction with a water-immiscible organic solvent such as ethyl acetate, chloroform, methylene chloride, methyl isobutyl ketone or a mixture of chloroform and methanol, preferably with chloroform/methanol (1:1, v/v). The organic phase is separated and dried to give an oily material. A non-polar organic solvent such as n-hexane is added to this oily material, the crude compounds being thus obtained in the form of powders.

The compounds obtained can be separated from each other by chromatography on columns packed with an adsorbent such as silica gel, or with a dextran gel such as Sephadex LH-20 and the like. Fractions are analysed by thin layer chromatography and/or high pressure liquid chromatography and the appropriate fractions are combined and evaporated to give the component in more or less pure form. Further purification may be carried out by repeated column chromatography and/or by high pressure liquid chromatography.

The acid hydrolysis of auramycin A or B or of sulfurmycin A or B in accordance with embodiment (b) of the foregoing process can be carried out in a manner known per se using an acid such as hydrochloric acid, sulphuric acid, phosphoric acid and the like (0.1-3 N). The hydrolysis may be carried out at a temperature of from 0° C. to the reflux temperature of the hydrolysis mixture, preferably at an elevated temperature. Auramycinone and sulfurmycinone, respectively, are prepared by this acid hydrolysis.

The splitting off of the sugar moiety from a compound of formula I' in accordance with embodiment (c) of the foregoing process can also be carried out in a manner known per se using a catalyst such as palladium, platinum, rhodium, activated nickel and the like, or an enzyme prepared, for example, from rat liver homogenates or cells of anthracycline antibiotic-producing microorganisms. 7-Deoxyauramycinone and 7-deoxysulfurmycinone, respectively, are prepared by this embodiment of the process.

The anthracyclinones and 7-deoxyanthracyclinones prepared according to the process provided by the present invention can be used as intermediates for the preparation of other anthracycline antibiotics, while auramycin A and B as well as sulfurmycin A and B exhibit antibacterial and antitumour activity. The conversion of the anthracyclinones into the corresponding anthracycline antibiotics can be effected by a process known per se, for example, the condensation of a suitably protected sugar halide with an anthracyclinone in an organic solvent such as 1,2-dichloroethane and the like in the presence of a metal catalyst such as silver carbonate, mercuric cyanide and the like (cf. F. Arcamone, "Topics in Antibiotic Chemistry, vol. 2" pages 156-171, 1978).

The 7-deoxyanthracyclinones may be converted to the anthracyclinones by following the procedures set forth in Examples 11 and 12 below. Thereafter the anthracyclinones can be converted into the corresponding anthracycline antibiotics by following the above referred to procedures. The subject matter of Examples 11 and 12 is added to the present specification for reference purposes only and does not form a part of the present invention.

Accordingly, the present invention is also concerned with antitumour agents which contain, as the active ingredient or active ingredients, auramycin A, auramycin B, sulfurmycin A and/or sulfurmycin B.

The biological activities of auramycin A and B and sulfurmycins A and B are as follows:

1. Table 6 hereinafter shows the in vitro minimum inhibitory concentrations (MIC) of auramycins A and B and sulfurmycins A and B in respect of various microorganisms determined using the agar streak method.

TABLE 6

| Strain | | MIC (µg/ml) | | | |
|---|---|---|---|---|---|
| | | Auramycin A | Auramycin B | Sulfurmycin A | Sulfurmycin B |
| Bacillus cereus | Ro 179B (1) | 0.39 | 0.2 | 0.2 | 0.39 |
| Bacillus subtilis | IAM 1027 (1) | 3.12 | 0.78 | 0.78 | 0.78 |
| Sarcina lutea | IAM 1009 (1) | 0.1 | 0.05 | 0.1 | 0.1 |
| Staphylococcus aureus 209P | IAM 1011 (1) | 1.56 | 0.39 | 0.78 | 0.78 |
| Staphylococcus aureus 209P Stf | | 0.78 | 0.39 | 0.2 | 0.39 |
| Staphylococcus epidermidis | IFO 12993 (1) | 3.12 | 1.56 | 3.12 | 1.56 |
| Micrococcus flavus | ATCC 10240 (1) | 0.1 | 0.05 | 0.2 | 0.1 |
| Mycobacterium smegmatis | IFO 13167 (1) | 6.25 | 3.12 | 25.0 | 6.25 |
| Escherichia coli K-12 | IAM 1264 (1) | >100 | >100 | >100 | >100 |
| Escherichia coli NIHJ | IFO 12734 (1) | >100 | >100 | >100 | >100 |
| Klebsiella pneumoniae | IFO 3512 (1) | >100 | >100 | >100 | >100 |
| Proteus vulgaris | IAM 1025 (1) | >100 | >100 | >100 | >100 |
| Pseudomonas aeruginosa | IFO 12689 (1) | >100 | >100 | >100 | >100 |
| Serratia marcescens | IFO 12648 (1) | >100 | >100 | >100 | >100 |
| Candida albicans | ATCC 10231 (2) | >100 | >100 | >100 | >100 |
| Candida tropicalis | ATCC 13803 (2) | >100 | >100 | >100 | >100 |
| Saccharomyces cerevisiae | ATCC 9763 (2) | >100 | >100 | >100 | >100 |

(1) Heart infusion agar
(2) Sabouraud dextrose agar

2. Acute toxicity

The acute intraperitoneal $LD_{50}$ in mice judged 72 hours after a single injection of the antibiotics is about 100 mg/kg for auramycin A, auramycin B and sulfurmycin A and 25-50 mg/kg for sulfurmycin B.

3. Antitumour effect

The anthracycline glycosides provided by the present invention were tested against P388 leukaemia in mice. When $CDF_1$ mice are inoculated with $1 \times 10^6$ cells of P388 intraperitoneally and each of the antibiotics is administered intraperitoneally on days 1, 5 and 9, the survival time of the treated mice is prolonged as shown in Table 7 hereinafter.

TABLE 7

| Antibiotic | Dose (mg/kg/day) | Mean survival (T/C, %) |
|---|---|---|
| Auramycin A | 15 | 170 |

TABLE 7-continued

| Antibiotic | Dose (mg/kg/day) | Mean survival (T/C, %) |
| --- | --- | --- |
|  | 7.5 | 134 |
|  | 3.75 | 129 |
|  | 1.88 | 139 |
| Auramycin B | 15 | 196 |
|  | 7.5 | 149 |
|  | 3.75 | 124 |
|  | 1.88 | 113 |
| Sulfurmycin A | 15 | 165 |
|  | 7.5 | 144 |
|  | 3.75 | 134 |
|  | 1.88 | 124 |
| Sulfurmycin B | 15 | 165 |
|  | 7.5 | 155 |
|  | 3.75 | 124 |
|  | 1.88 | 124 |

As mentioned earlier, auramycin A, auramycin B, sulfurmycin A and sulfurmycin B can be used as medicaments against tumours in the form of pharmaceutical preparations. The present antitumour agents also include the pharmaceutically acceptable salts of these compounds.

The present pharmaceutical preparations contain the active ingredient in association with a compatible pharmaceutical carrier. This carrier can be an organic or inorganic inert carrier material suitable for enteral, percutaneous or parenteral administration such as, for example, water, gelatin, gum arabic, lactose, starch, magnesium stearate, talc, vegetable oils, polyalkyleneglycols, petroleum jelly and the like. The pharmaceutical preparations may also contain therapeutically valuable materials other than auramycin A, auramycin B, sulfurmycin A and/or sulfurmycin B. The pharmaceutical preparations can be made up in a solid form (e.g. as tablets, dragées or capsules) or in a liquid form (e.g. as solutions, suspension or emulsions). The pharmaceutical preparations may be sterilised and/or may contain adjuvants such as preservatives, stabilisers, wetting agents, emulsifiers, salts for varying the osmotic pressure or buffers.

The dosage in which the active ingredient is administered depends on the route of administration, the age, weight and condition of the patient and the particular disease to be treated. However, a typical dosage for adults is in the range of 20 mg to 30 mg per day in the case of oral or parenteral administration, preferably by intravenous injection.

The following Examples illustrate the process provided by the present invention:

EXAMPLE 1

The scraped spores from an agar slant of *Streptomyces galilaeus* OBB-111 were transferred to a 500 ml Erlenmeyer flask containing 100 ml of sterilised medium consisting of 20.0 g of D-glucose, 20.0 g of soluble starch, 5.0 g of S-3 meat (Ajinomoto Co., Ltd.), 2.5 g of yeast extract (Daigo Eiyo-Kagaku Co., Ltd.), 1.0 g of dipotassium hydrogen phosphate, 1.0 g of magnesium sulphate heptahydrate, 3.0 g of sodium chloride and 3.0 g of calcium carbonate made up to 1 liter with tap water. This vegetative culture was incubated at 27° C. on a rotary shaker set at 180 revolutions per minute. After 72 hours, 2 ml of the culture were transferred to a 500 ml Erlenmeyer flask containing 100 ml of sterile production medium consisting of 20.0 g of D-glucose, 20.0 g of soluble starch, 10.0 g of Pharmamedia (Traders Oil Mill Co., USA), 1.0 g of dipotassium hydrogen phosphate, 1.0 g of magnesium sulphate heptahydrate, 3.0 g of sodium chloride and 3.0 g of calcium carbonate made up to 1 liter with tap water. The culture was incubated at 27° C. for 72-96 hours on a rotary shaker set at 180 revolutions per minute.

At this time antibiotic activity of the culture filtrate and the mycelial extract, measured by the paper disc agar diffusion method using *Sarcina lutea* IAM-1009 as a test microorganism, was 22 mm and 20 mm in diameter, respectively.

EXAMPLE 2

(a) 600 ml of the vegetative culture obtained in a manner analogous to that as described in Example 1 were transferred to a 50 liter jar containing 30 liters of sterile production medium containing the same components as described in Example 1 and including 0.1% Nissan Disfoam (Nippon Yushi Co., Ltd.). The cultivation was carried out at 27° C. with an agitation of 350 revolutions per minute and aeration 1 v/v medium. After approximately 90 hours, the incubation was terminated.

(b) The culture was then centrifuged. The filtrate and the filter cake thus obtained were extracted separately. The filter cake was suspended in 15 liters of methanol, stirred for 3 hours and filtered, the resulting filter cake was again extracted with methanol. 30 liters of chloroform and 30 liters of water were added to and mixed with the resulting extract and the chloroform layer was separated. On the other hand, the culture filtrate was extracted with 60 liters of a solvent mixture of chloroform and methanol (1:1) and the chloroform layer was separated. The chloroform extracts from the cell cake and the culture filtrate were combined and evaporated to a small volume (50-60 ml). The concentrate was diluted with n-hexane to precipitate a yellow solid which was dried in vacuo to give 4.8 g of a mixture of auramycin A, auramycin B, sulfurmycin A, sulfurmycin B, auramycinone, sulfurmycinone, 7-deoxyauramycinone and 7-deoxysulfurmycinone.

(c) Fractionation of the foregoing mixture was carried out. Sephadex LH-20 soaked for 15 hours in a solvent mixture of chloroform and methanol (2:1, v/v) was packed into a column of 50 cm length and 5.0 cm diameter. The mixture obtained according to the preceding paragraph (4.8 g) was dissolved in 10 ml of a mixture of chloroform and methanol (2:1, v/v) and applied to the column. The column was eluted with a mixture of chloroform and methanol (2:1, v/v). As a result, two distinct bands of anthracyclines were noted. One was shown by thin layer chromatography on silica gel (chloroform/methanol, 19:1, v/v) to be a mixture mainly of 7-deoxyauramycinone and 7-deoxysulfurmycinone with small amounts of auramycinone and sulfurmycinone. The fractions containing this mixture was concentrated to dryness in vacuo and 1.2 g of a yellow solid were obtained. The other band eluted was found to contain the anthracycline glycosides. The fractions containing these glycosides were concentrated to dryness in vacuo to yield 2.1 g of a yellow solid.

(d) The yellow solid (2.1 g) containing auramycins A and B and sulfurmycins A and B was dissolved in a small amount of chloroform and applied to a column of 40 cm length and 2.5 cm diameter packed with silica gel. After washing the column with chloroform, auramycin B was eluted. Sulfurmycin B and auramycin A were eluted with a 98:2 (v/v) chloroform/methanol mixture. Then, sulfurmycin A was eluted with a 95:5

(v/v) chloroform/methanol mixture. This fraction was contaminated with a small amount of auramycin A. Each of the eluates was concentrated to dryness in vacuo, there being obtained 150 mg of crude auramycin B, 260 mg of a mixture of auramycin A and sulfurmycin B and 160 mg of a mixture of auramycin A and sulfurmycin A, respectively, in the form of yellow powders.

(e) The crude auramycin B (150 mg) obtained in step (d) was further purified by preparative liquid chromatography. The sample was dissolved in 5 ml of a solvent mixture of methylene chloride and methanol (99:1, v/v) and chromatographed on Prep PAK-500/SILICA (waters Associates, Inc.). The mobile phase was a 99:1 (v/v) mixture of methylene chloride and methanol at a flow rate of 50 ml/minute. The elution was monitored using a refractive index monitor. The fractions containing only auramycin B (thin layer chromatography on silica gel; chloroform/methanol, 29:1, v/v) were collected and concentrated in vacuo to a small volume. Addition of some n-hexane caused precipitation of 98 mg of pure auramycin B.

(f) The mixture of sulfurmycin B and auramycin A (260 mg) obtained in step (d) was purified by the method described in step (e). The mobile phase was a methylene chloride/methanol mixture (197:3, v/v) at a flow rate of 50 ml/minute. Sulfurmycin B fractions were eluted first and auramycin A fractions next. The fractions containing pure sulfurmycin B and auramycin A were concentrated in vacuo to small volumes. Addition of n-hexane to the concentrates yielded 122 mg of pure sulfurmycin B and 54 mg of pure auramycin A, respectively.

(g) The mixture containing auramycin A and sulfurmycin A (160 mg) obtained in step (d) was purified by the method described in step (e). The mobile phase was methylene chloride/methanol (98:2, v/v) at a flow rate of 50 ml/minute. The first fractions contained a small amount of auramycin A and were followed by the sulfurmycin A fractions. The fractions containing pure sulfurmycin A were concentrated in vacuo to a small volume and yielded 68 mg of pure sulfurmycin A upon addition of a small quantity of n-hexane.

(h) 1.2 g of the yellow solid consisting mainly of 7-deoxyauramycinone and 7-deoxysulfurmycinone and of minor amounts of auramycinone and sulfurmycinone obtained in step (c) were mixed with silica gel and subjected to column chromatography on silica gel (column 25×2.5 cm) using a mixture of chloroform and n-hexane (4:1, v/v) as eluant. 7-Deoxysulfurmycinone was eluted first followed by 7-deoxyauramycinone, sulfurmycinone and auramycinone in this order. The fractions containing only one compound were concentrated to dryness in vacuo. 43 mg of pure 7-deoxysulfurmycinone, 68 mg of 7-deoxyauramycinone, 5 mg of sulfurmycinone and 7 mg of auramycinone, respectively, were thus obtained in the form of yellow powders.

EXAMPLE 3

In a manner analogous to that described in Example 2, using wheat germ as a nitrogen source and *Streptomyces galilaeus* OBB-111-610, obtained by treating *Streptomyces galilaeus* OBB-111 with N-methyl-N-'-nitro-N-nitrosoguanidine, there were obtained 153 mg of auramycin B, 171 mg of sulfurmycin B, 137 mg of auramycin A, 149 mg of sulfurmycin A, 55 mg of 7-deoxysulfurmycinone, 78 mg of 7-deoxyauramycinone, 5 mg of sulfurmycinone and 7 mg of auramycinone.

EXAMPLE 4

In a manner analogous to that described in Example 2, using *Streptomyces galilaeus* FR-401, there were obtained 14 mg of auramycin B, 16 mg of sulfurmycin B, 13 mg of auramycin A, 14 mg of sulfurmycin A, 5 mg of 7-deoxysulfurmycinone and 5 mg of 7-deoxyauramycinone.

EXAMPLE 5

A solution of 100 mg of auramycin A in 20 ml of 0.1 N hydrochloric acid was heated at 90° C. for 60 minutes. The mixture was cooled and extracted with 40 ml of ethyl acetate. The ethyl acetate layer obtained was dehydrated over sodium sulphate and concentrated in vacuo to give 40 mg of a yellow powder. Crystallisation from n-hexane/chloroform gave 30 mg of auramycinone (yellow needles).

EXAMPLE 6

A solution of 100 mg of sulfurmycin A in 20 ml of 0.1 N hydrochloric acid was heated at 90° C. for 60 minutes. The mixture was cooled and extracted with 40 ml of ethyl acetate. The ethyl acetate layer obtained was dehydrated over sodium sulphate and concentrated in vacuo to give 45 mg. of a yellow powder. Crystallisation from n-hexane/chloroform gave 32 mg of sulfurmycinone (yellow needles).

EXAMPLE 7

A solution of 300 mg of a mixture of anthracycline glycosides, obtained by a process similar to that described in step (c) of Example 2 in 20 ml of 0.1 N hydrochloric acid was heated at 90° C. for 60 minutes. The mixture was cooled and extracted with 80 ml of ethyl acetate. The ethyl acetate layer was dried over sodium sulphate and concentrated in vacuo to give 50 mg of a yellow powder containing sulfurmycinone and auramycinone. The mixture of anthracyclinones was mixed with silica gel and subjected to column chromatography on silica gel (column 30×2.5 cm) with methylene chloride. Sulfurmycinone was eluted first and auramycinone next. The fractions containing sulfurmycinone were combined and concentrated in vacuo to dryness to yield 24 mg of sulfurmycinone in the form of a yellow powder. The fractions containing auramycinone were combined and concentrated in vacuo to dryness to yield 11 mg of auramycinone in the form of a yellow powder.

EXAMPLE 8

Ten male Wister rats were sacrificed by decapitation. Livers were excised and homogenized with a glass Teflon homogeniser in 300 ml of 0.15 M potassium chloride solution and centrifuged at 9000×G for 10 minutes. The supernatant liquid was used for an enzyme preparation. A mixture consisting of 40 ml of enzyme preparation, 2 ml of a solution of auramycin A (10 mg/ml), 10 mg of NADPH and 5 ml of 0.1 M Tris-HCl buffer (pH 7.8) was left to stand at 37° C. for 45 minutes anaerobically. The reaction was terminated by the addition of a solvent mixture of chloroform and methanol (1:1, v/v). The chloroform layer was separated, concentrated in vacuo and chromatographed by thin layer chromatography (toluene/methanol=20:1, v/v). The band containing 7-deoxyauramycinone was scraped off, extracted with chloroform and concentrated in vacuo to dryness. 2.5 mg of 7-deoxyauramycinone were obtained.

EXAMPLE 9

In a manner analogous to that described in Example 8, using 20 mg of sulfurmycin A, there were obtained 2.3 mg of 7-deoxysulfurmycinone.

EXAMPLE 10

Enzymatic hydrogenolysis of auramycin A, auramycin B, sulfurmycin A and sulfurmycin B.

A 500 ml Erlenmeyer flask with 100 ml of vegetative culture of *Streptomyces galilaeus* OBB-111, obtained by a process analogous to that described in Example 1, containing auramycin A, auramycin B, sulfurmycin A and sulfurmycin B, was allowed to stand at room temperature for 12 hours and extracted with 200 ml of a solvent mixture of chloroform and methanol (1:1, v/v). The chloroform layer was separated, concentrated in vacuo and chromatographed by thin layer chromatography (toluene/methanol=20:1, v/v). The bands containing 7-deoxysulfurmycinone and 7-deoxyauramycinone were scraped off, extracted with chloroform and concentrated in vacuo to dryness to give 1.4 mg of pure 7-deoxysulfurmycinone and 1.2 mg of pure 7-deoxyauramycinone, respectively.

EXAMPLE 11

To 40 ml of carbon tetrachloride was added 38.2 mg (0.1 mmol) of 2β-methyl-1,2,3,4,6,11-hexahydro-2α,5,7-trihydroxy-6,11-dioxo-1-naphthacenecarboxylic acid methyl ester, and the mixture was heated to effect solution. After cooling to 25° C., the solution was treated with 20 mg (0.112 mmol) of N-bromosuccinimide, 80 μl distilled water and 5 mg of 2,2'-azobis-(2-methylpropionitrile), catalyst. This mixture was heated under reflux for 0.5 hr an an additional 5 mg (0.0281 mmol) of N-bromosuccinimide was added. After a further 0.25 hr of reflux period, the reaction was cooled to room temperature and treated with 50 ml of tetrahydrofuran and 25 ml of 10% potassium carbonate. The mixture was stirred for 10 minutes and then partitioned between 1 N hydrochloride acid/methylene chloride. The aqueous phase was further extracted 3× with methylene chloride. The organic extracts were dried over sodium sulfate and evaporated to yield crude residue. The product was further purified by thick layer chromatography over silica, eluting with methylene chloride 93/acetone 7, yielding pure 2β-methyl-1,2,3,4,6,11-hexahydro-2α,-4α,5,7-tetrahydroxy-6,11-dioxo-1-naphthacenecarboxylic acid methyl ester, m.p. 163°-165° C. (abs. ethanol).

EXAMPLE 12

A solution of 42.4 mg (0.1 mmol) of 2β-(2-oxopropyl)-1,2,3,4,5,11-hexahydro-2α,5,7-trihydroxy-6,11-dioxo-1-naphthacenecarboxylic acid methyl ester in 40 ml of carbon tetrachloride was treated with 80 μl of distilled water, 20 mg (0.112 mmol) of N-bromosuccinimide, and 5 mg of 2,2'-azobis-(2-methylpropionitrile). The mixture was heated under reflux for 0.5 hr and then treated with an additional 5 mg of NBS. After 15 min, the reaction was cooled, 50 ml of tetrahydrofuran/25 ml of 10% potassium carbonate was added, and the mixture was stirred for 10 min at 25°. The product was partitioned between N sulfuric acid/methylene chloride, and the organic phases were dried over sodium sulfate and evaporated to afford the crude residue. The product was isolated by thick layer chromatography over silica, eluting 2× with toluene/CH₃OH, 25:1, to afford 2β-(2-oxopropyl)-1,2,3,4,6,11-hexahydro-2α,-4α,5,7-tetrahydroxy-6,11-dioxo-1-naphthacenecarboxylic acid methyl ester, m.p. 159°-160° C. (EtOAc/Pet. Ether).

We claim:

1. A compound of the formula

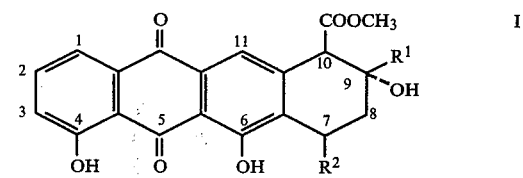

wherein $R^1$ represents a methyl or acetonyl group and $R^2$ represents a group of the formula

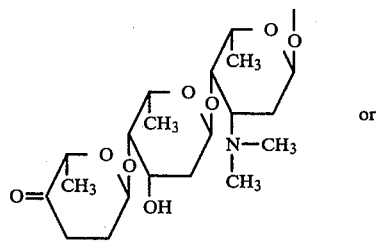

2. The compound of claim 1 wherein $R^1$ is methyl and $R^2$ is

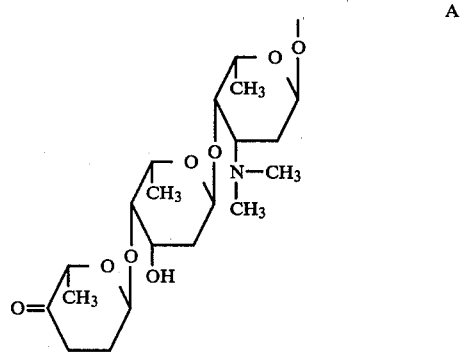

3. The compound of claim 1 wherein $R^1$ is acetonyl and $R^2$ is

5. The compound of claim 1 wherein $R^1$ is acetonyl and $R^2$ is

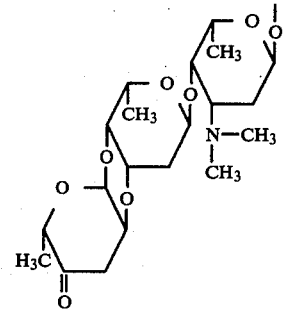
A

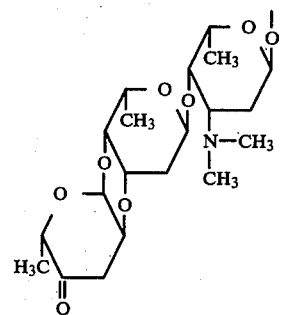
B

4. The compound of claim 1 wherein $R^1$ is methyl and $R^2$ is

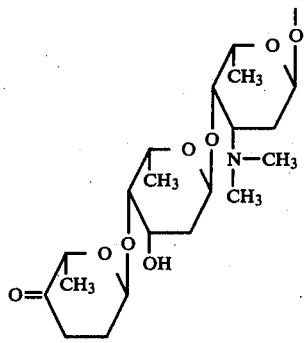
B

6. A pharmaceutical composition useful in the treatment of bacterial infections which comprises as an active ingredient a compound selected from the group consisting of auramycin A, auramycin B, sulfurmycin A and sulfurmycin B in combination with a pharmaceutically compatible carrier.

* * * * *

UNITED STATES PATENT AND TRADEMARK OFFICE
CERTIFICATE OF CORRECTION

PATENT NO. : 4,329,339

DATED : May 11, 1982

INVENTOR(S) : Akiko Fujiwara, Tatsuo Hoshino and Masaaki Tazoe

It is certified that error appears in the above—identified patent and that said Letters Patent is hereby corrected as shown below:

After "[22]   Filed:      May 21, 1980" add on cover page

— Foreign Application Priority Data

May 22, 1979      Great Britain.................... -- 17763/79 --.

Signed and Sealed this

Third Day of August 1982

[SEAL]

*Attest:*

GERALD J. MOSSINGHOFF

*Attesting Officer*   *Commissioner of Patents and Trademarks*